(12) United States Patent
Chu

(10) Patent No.: US 7,392,953 B2
(45) Date of Patent: Jul. 1, 2008

(54) PROGRAMMABLE DIGITAL LABELS

(75) Inventor: Victor Chu, New York, NY (US)

(73) Assignee: Mil. Digital Labeling, Inc., New York, NY (US)

(*) Notice: Subject to any disclaimer, the term of this patent is extended or adjusted under 35 U.S.C. 154(b) by 0 days.

(21) Appl. No.: 11/371,530

(22) Filed: Mar. 9, 2006

(65) Prior Publication Data

US 2006/0202042 A1    Sep. 14, 2006

Related U.S. Application Data

(60) Provisional application No. 60/660,500, filed on Mar. 10, 2005.

(51) Int. Cl.
*G06K 19/06*    (2006.01)
(52) U.S. Cl. .......................... 235/492; 235/380

(58) Field of Classification Search .................. 235/487, 235/492, 380, 375
See application file for complete search history.

(56) References Cited

U.S. PATENT DOCUMENTS

| 6,753,830 B2 | 6/2004 | Gelbman | |
| 2007/0024551 A1* | 2/2007 | Gelbman | ...................... 345/85 |

* cited by examiner

*Primary Examiner*—Karl D. Frech
(74) *Attorney, Agent, or Firm*—Coats & Bennett, P.L.L.C.

(57) ABSTRACT

A label for a product includes an electronic display for displaying label information. The digital label includes an operating system program with an applications interface to allow development of custom applications by manufacturers, retailers, and users of the product. The digital label also includes a communications interface enable communication with external devices, such as other computer systems. The processor in the digital label can process, display, and transmit information.

42 Claims, 9 Drawing Sheets

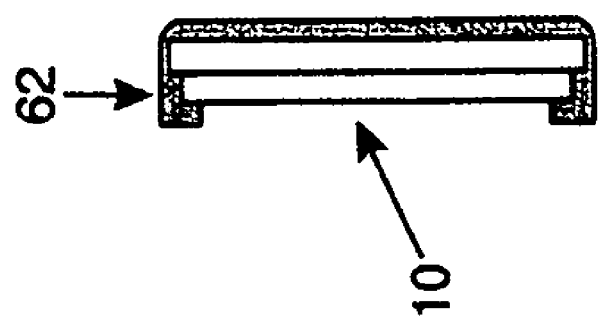
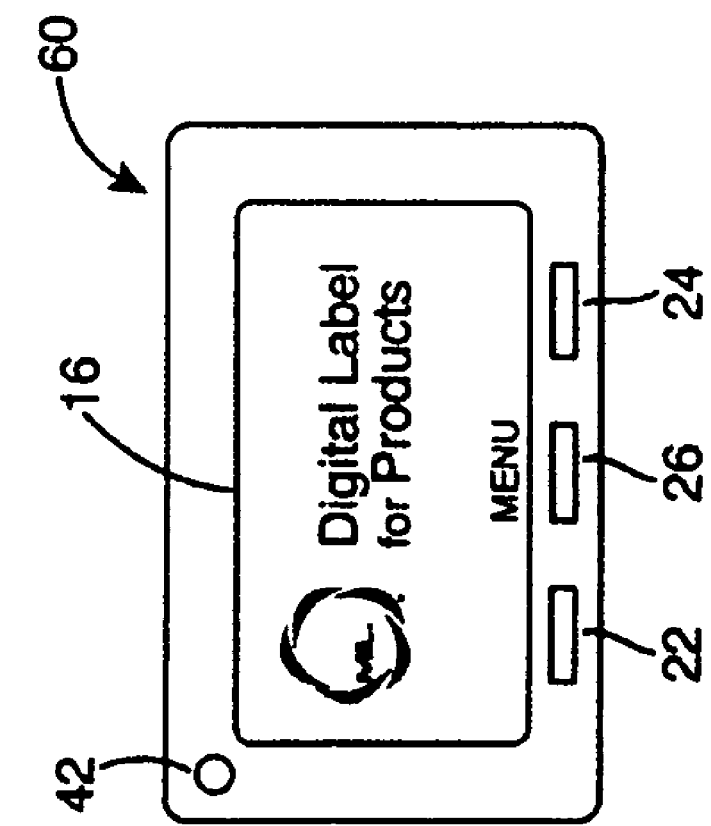
FIG 2
FIG 3

PROGRAMMABLE DIGITAL LABELS

RELATED APPLICATIONS

This application claims benefit of U.S. Provisional Application Ser. No. 60/660,500 filed Mar. 10, 2005 entitled "Transmittable Digital Product and Label Data," which is incorporated herein by reference.

BACKGROUND OF THE INVENTION

The present invention relates generally to the field of digital labels and tags for products. It is typical for the manufacturer of a product to affix a label to the product which bears the manufacturer's brand name or logo. Labels are also used to provide product information and information about the manufacturer of the product. Because labels are typically small, they can carry only a limited amount of information. Therefore, it is not at all uncommon to find two or more labels affixed to different locations of a single product. For example, a product may carry a brand label which is placed in a visible location, and interior labels to give product information. However, there is a small, finite limit to the number of labels which can be applied to a product without cluttering the product.

In the past, labels have served as merely static and passive devices to convey label information that is fixed in time, and have not been used to expand the functionality of the product. Animated designs and logos are not possible with conventional woven, printed or stamped labels. Also, conventional labels cannot display information which may change over time, or user-specific information.

SUMMARY OF THE INVENTION

The present invention is a digital label for products that can be programmed to store, process, transmit and display information including label information and user-specific information. The digital label can also store authentication data to authenticate the product. The digital label includes a processing circuit, a memory for storing label information, and a display for displaying label information. An extensible program is stored in memory and is configured to execute user-defined applications or program code to extend the functionality of the digital label. In one embodiment of the invention, the extensible program comprises an operating system program with an application interface that allows development of custom applications by the manufacturer, retailer, or user to expand the functionality of the digital label. User-defined applications enable the digital label to receive, store, and process user-specific information, and to communicate and work other devices.

BRIEF DESCRIPTION OF THE DRAWINGS

FIG. 2 is a front view of an exemplary digital label.

FIG. 3 is a side view of an exemplary digital label contained in a secondary encasement, which is shown in section.

DETAILED DESCRIPTION OF THE DRAWINGS

Figure 1:
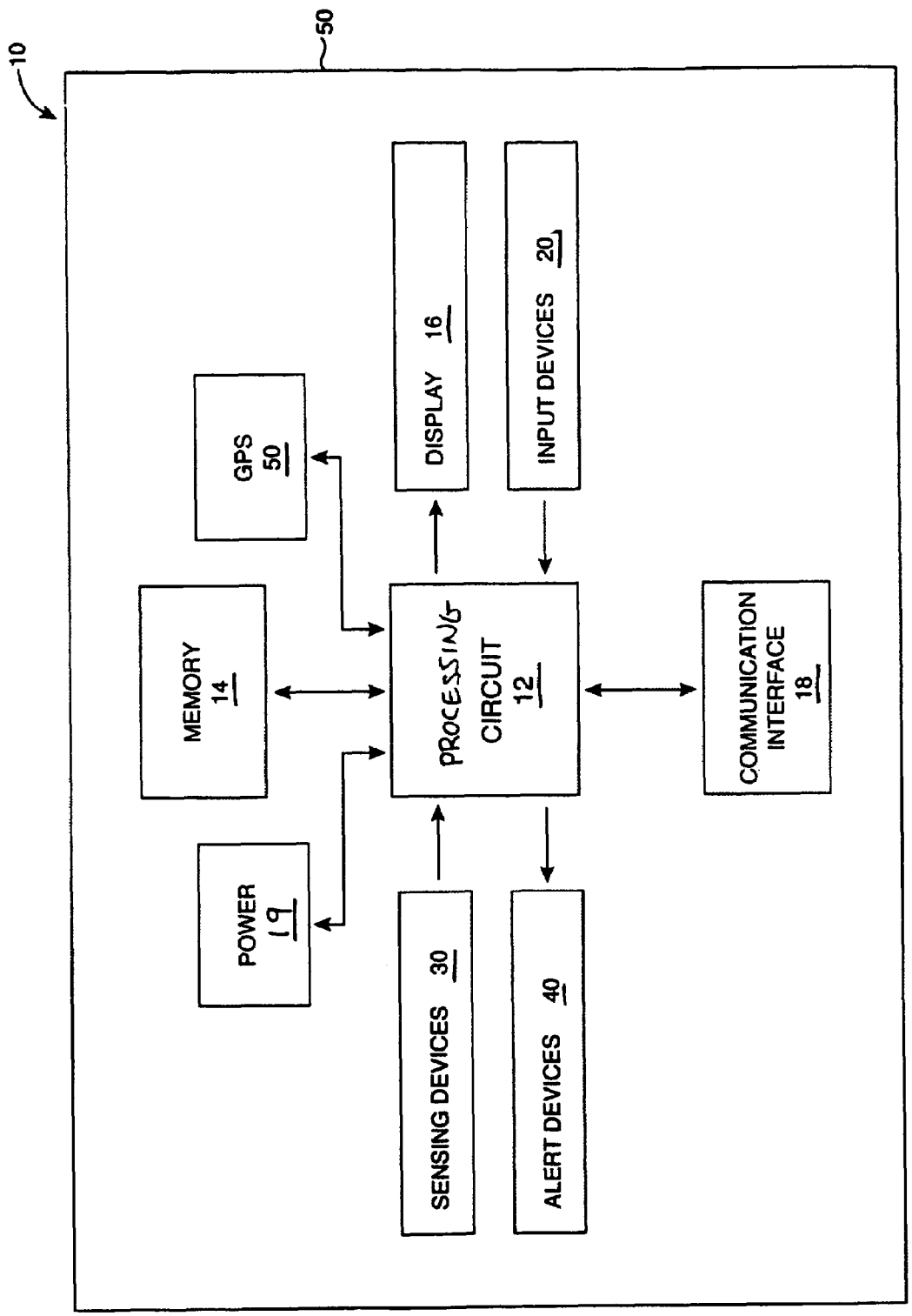
FIG. 1 is a functional block diagram of an exemplary digital label.

Referring now to the drawings, and particularly to FIG. 1, a digital label 10 for products is shown and indicated generally by the numeral 10. For purposes of this application, the term "digital label" means a device having a display that functions principally as a means of identification that is attached or affixed to a product to designate its origin, owner, manufacturer, contents or ingredients, use, etc. The term "label" is used in the common sense to mean a device that is distinguishable from the product to which it is affixed and not a typical or inherent feature of the product. For example, a computer monitor and a display for a consumer electronic device (e.g., watch, cell phone, camera, etc.) are not considered to be "labels' as that term is used herein because the displays are inherent product features.

The digital label 10 stores and displays label information and other information as more fully described below. The term "label information" includes source information indicating the source or origin of the product, product information describing the features contents, ingredients or use of the product, and manufacturer information that provides information about the product manufacturer. An example of source information is a brand name, logo (including animated logos), or slogan which identifies the source or origin, and authentication data for verifying the authenticity of the product. Examples of product information are instructions for the care or use of the product, and description of the contents or ingredients of the product. Examples of manufacturer information are the address (including an e-mail address) or telephone number for contacting the manufacturer, and the IP address of a web page for finding additional information about the company and its products.

The digital label may also store consumer information or user information in addition to label information, and perform custom functions for the user. Consumer information is personal user information that affects the ownership, history, usage and effectiveness of the product. Examples of personal information are registration data, such as the name, address, contact information, weight, height, age, birth date, sex, DNA, allergies, medical and health conditions and history, scheduling information, personal preferences, diet, account information, other product usage data, etc.

The digital label 10 is particularly useful for products that do not otherwise include a display or microprocessor as an inherent feature of the product, but may also be used on products with a display or microprocessor. For example, in products that include a display as a functional feature of the product, the manufacturer may still use the digital label 10 of the present invention to provide a separate, dedicated display or microprocessor for displaying and transmitting trademarks, logos, brands, slogans, or other label and product information.

The digital label 10 according to the present invention provides a platform for manufacturers, retailers and end users to develop custom applications for the digital label 10 to expand the functionality of the digital label 10. In one embodiment, a processing circuit is configured to recognize and execute the user-defined applications. As used herein, the term "user-defined" refers to users of the label and includes product manufacturers, retailers, and end users of the product. The user-defined applications allow the functionality of the digital label 10 to be expanded to perform functions for the user. Thus, the present invention extends the concept of a product label to include active devices that do more than present static information. The digital labels 10 according to various embodiments function as small computing devices that can be programmed to perform a wide variety of functions.

FIGS. 1 and 2 illustrate the main components of the digital label 10 according to one exemplary embodiment. The digital label 10 comprises a processing circuit 12, memory 14, display 16, a communications interface 18, and a battery 19 to provide power for the digital label 10. The processing circuit 12 controls the overall operation of the digital label 10 according to program instructions stored in memory 14 and may comprises one or more digital processing devices, such as microprocessors, microcontrollers, hardware, firmware, or a combination thereof. Memory 14 stores program instructions and data needed for operation. An extensible program (FIG. 4) stored in memory 14 controls the basic functions of the digital label 10. As described in greater detail below, the extensible program is configured to execute custom applications or custom program code stored in memory 14 to expand the functionality of the digital label 10. The display 16 may comprise a liquid crystal display (LCD) or an organic light emitting diode (OLED). Additionally, the display 16 may use printed electronic displays, electronic paper displays, or electronic ink technology provide a thin, flexible and durable display to enable users to view information. The communications interface 18 may comprise a short-range wireless interface, such as a BLUETOOTH interface, ZIGBEE, or WIFI interface, a long range cellular phone or satellite communications interface, or a wired interface, such as a RS 232, USB or FIREWARE interface. There may be more than one communications interface 18.

Some embodiments of the digital label 10 may additionally include one or more user input devices indicated generally by the numeral 20. User input devices 20 for the digital label 10 may comprise any known input device including buttons, keypads, touch pads, wheels, dials, mouse devices, trackballs, etc. A touch screen display could also be used for user input. Imaging systems and motion or movement systems for recognizing hand gestures, and voice recognition systems may also be used for receiving user input. In FIG. 2, three soft keys denoted by the numerals 22, 24, 26 are provided to receive user input. The soft keys 22, 24, 26 may have different functions depending on the current context. The function of the soft keys 22, 24, 26 may be displayed to the user on display 16 when the soft keys 22, 24, 26 are active. For example, the middle key 26 shown in FIG. 2 has the text MENU displayed above the key 26 on the display 16. Pressing the soft key 26 in this context will invoke an onscreen menu. In some embodiments, more sophisticated user input devices can be used to enable users to input user information.

The digital label 10 may include or receive input from one or more sensors or detectors 30 that sense environmental conditions such as temperature, pressure and humidity; or product characteristics, such as size, volume, weight of the product, or chemical changes in the product. Sensors or detectors 30 may also be used to detect product usage and/or tampering. Sensors or detectors 30 for the digital label 10 may also detect location, distance or proximity. The digital label 10 may incorporate a GPS receiver 50 or other location detector to determine location and history of locations. Clocks and counters may provide additional input to the processing circuit 12. Those skilled in the art will appreciate, however, that the processing circuit 12 may include internal clocks and counters.

The digital label 10 may include or control one or more alerting devices 40 for alerting the user of specified events or conditions. The alerting devices 40 may comprise indicator lights that illuminate or generate lighting effects; speakers, beepers, buzzers, or other sound devices; and vibrators or other tactile devices. The digital label 10 could also play MP3 or other audio files to alert the user. The alerting devices 40 are controlled by the system processor to notify the user when predetermined events or conditions occur. The alerts can be personalized and customized by the user to distinguish the alerts. FIG. 2 illustrates an indicator lamp 42 that is used as an alerting device 40.

The digital label 10 may include a primary casing 60 to house the components of the digital label 10. The primary casing 60 is preferably waterproof or water-resistant to protect the components. The primary casing 60 should also be impact resistant and shock-resistant. The casing 60 may be constructed of plastic, rubber, metal, ceramic, or other materials or organic, environmentally friendly protein based material that is easily recycled or returned to the earth. In some embodiments, the digital label 10 can be integrated with a product or product container or product packaging. In still other embodiments, a secondary encasement 62 can also be used that allows the digital label 10 to be removed from the product as shown in FIG. 3. This can enable the user to take the digital label 10 with them to interact, monitor and control the product remotely.

Any suitable method of attaching the digital label 10 to the product may also be used. For example, the digital label 10 or secondary encasement 62 may be secured to products by adhesives, by magnets, by sewing or stitching, by sonic welding laser welding or heat welding, by VELCRO-type fasteners, or by mechanical fasteners such as hooks, screws, buckles, zippers, snaps, or pins. The digital label 10 could also be entrapped or retained by other features of the product which function as the secondary encasement 62. For example, the label 10 could be designed as a cartridge which slides in a pocket or pouch on the product or snapped into the product and released by a mechanism. The digital label 10 may also be suspended from or secured to the product by means of a hanger, strap or cord that passes though an opening (not shown) in the casing 60.

Figure 4:
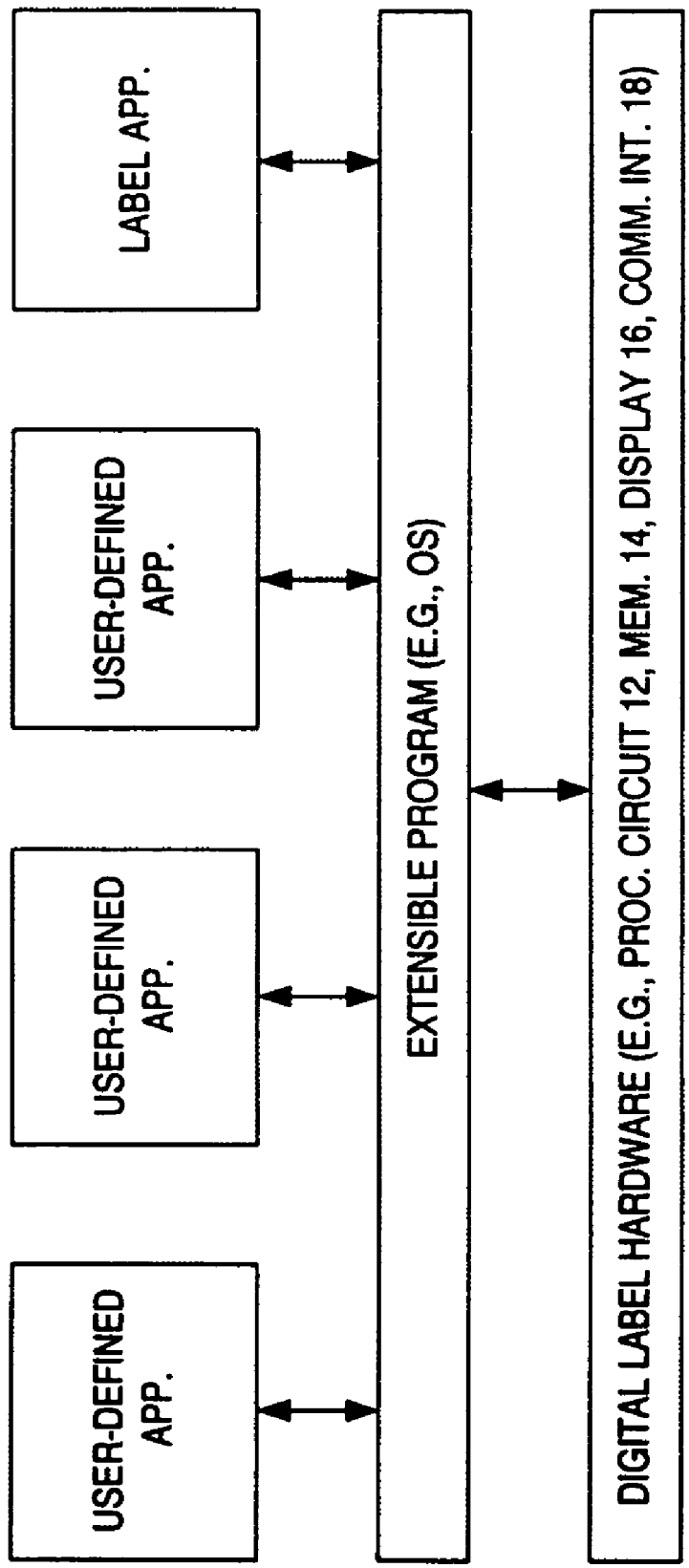
FIG. 4 illustrates an exemplary software architecture for the digital label.

FIG. 4 illustrates the relationship of the extensible program with other elements of the digital label 10. The extensible program may comprise, for example, an operating system program with an application interface (API) to enable manufacturers, retailers, and end users to develop custom applications for the digital label 10. The operating system may, for example, be an embedded operating system such as Windows CE, Symbian, QNX, or embedded Linux. A proprietary operating system could also be used. A label application for managing and displaying label information can be preloaded and stored in the memory 104 of the digital label 10 by the label manufacturer. Additional user-defined application programs can be input and stored to add additional functions to the digital label 10 by the product manufacturer, by retailers of the products, or by end users of the products. The custom application programs can be input via one of the communication interfaces 18. The operating system or other extensible program is able to execute the custom applications developed by the product manufacturer, retailer, or end user. The type of functions that can be performed by custom applications is virtually unlimited. For example, the application programs can perform functions such as product authentication, location tracking, scheduling, usage tracking, etc.

Figure 5:
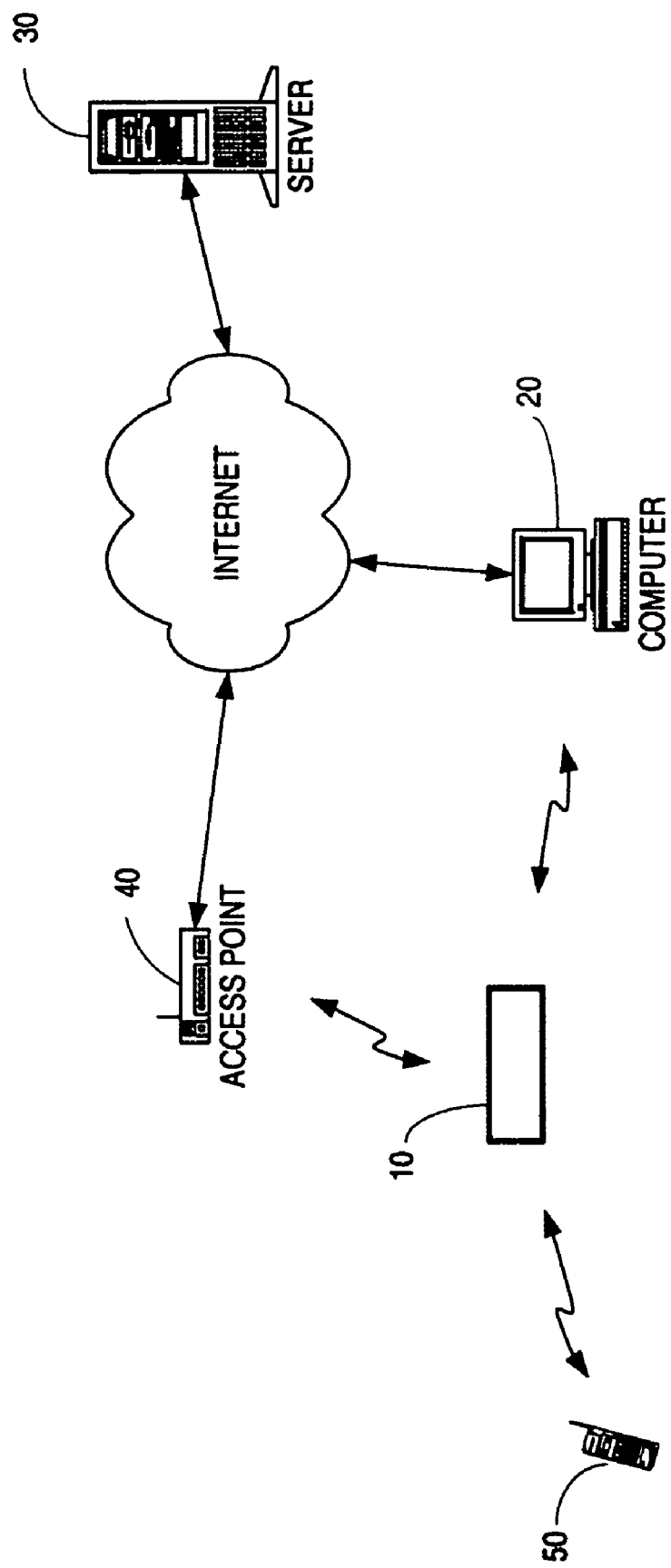
FIG. 5 illustrates the digital label communicating with other devices in a network environment.

One advantage of the digital label 10 is its ability to communicate and share information with other devices. The digital label 10 may have its own IP address assigned so that it can communicate directly with other devices across the Internet. FIG. 5 illustrates different ways the digital label 10 can communicate with other devices. FIG. 5 illustrates a local computer 110, a web-based server system 120, and a cell phone or PDA 140. The digital label 10 communicates with the local computer 110 over a local area network. The digital label 10 may communicate with a web-based server system 120 by connecting to a web access point 130. The digital label 10 may also communicate with the cell phone or PDA 140, using a standard cellular or satellite transceiver.

The digital label 10 may store, process and communicate user information. The user information may be entered directly by the user or may be transferred over the communications interface 18 to the digital label 10. For example, the digital label 10 may collect information about the use of the product and store the information for subsequent viewing and analysis. The digital label 10 may generate history reports that can be viewed by the user on the display 16 or transferred to other devices. Also, label information stored in the digital label 10 at the time of purchase by the customer can be updated via the communications interface 18.

The variety of applications that can be developed for the digital label is virtually limitless. A few exemplary applications for the digital label 10 are described below.

EXAMPLE 1

Tag for Authentication and Product Tracking

A recurring problem with branded and successful goods, such as designer and luxury clothing, handbags, accessories, jewelry, luggage; medication, liquor, and replacement parts, is the prevalence of counterfeit goods. As noted above, the digital label 10 of the present invention may store authentication data that enables purchasers of such goods to verify the authenticity of the products they purchase. The authentication data may comprise, for example, a serial number or code that can be used by the purchaser to authenticate genuine products. In some exemplary embodiments, the authentication data may be encrypted with a secret code to prevent counterfeiters from duplicating digital labels 10. The authentication data may also change over time to make it more difficult to mimic. The digital label 10 may also include a GPS receiver to enable tracking of the product in case that the product is lost or stolen.

Figure 6:
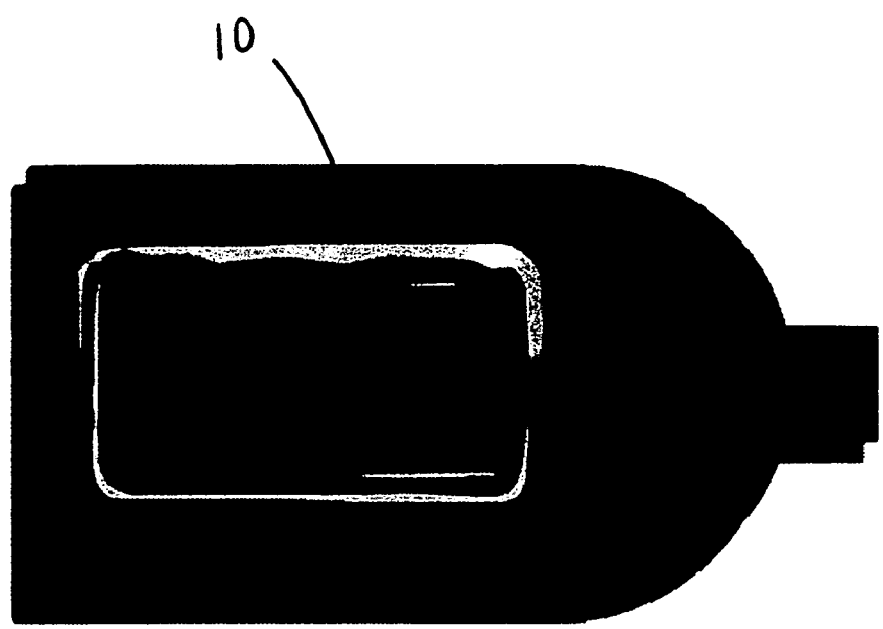
FIG. 6 illustrates a tag for products incorporating a digital label.

FIG. 6 illustrates a tag including a digital label 10 for products such and luggage, handbags, and brief cases. The digital label 10 stores an authentication number or serial number in memory 14 to enable users to authenticate genuine goods. The memory 14 for storing the authentication data may be a secure, tamper-proof memory to prevent tampering. The serial number may also be encrypted by the manufacturer with a secret key. For example, the serial number may be encrypted or signed with the manufacturer's private key and can be verified by the user by decrypting the serial number using the manufacturer's corresponding public key, which can be obtained from the manufacturer's web site. If the authentication data is successfully decrypted, the user can be confident that the product is a genuine product so long as the manufacturer's private key has not been compromised. The user can also verify the authenticity of the product by sending the serial number to the manufacturer during product registration for verification. The authentication number could be read by the user from the digital label 10, or could be transmitted from the digital label 10 to the user's computer or other device. In some embodiments, the digital label 10 could transmit the authentication number via the Internet to a server maintained by the manufacturer for verification.

Figure 7:
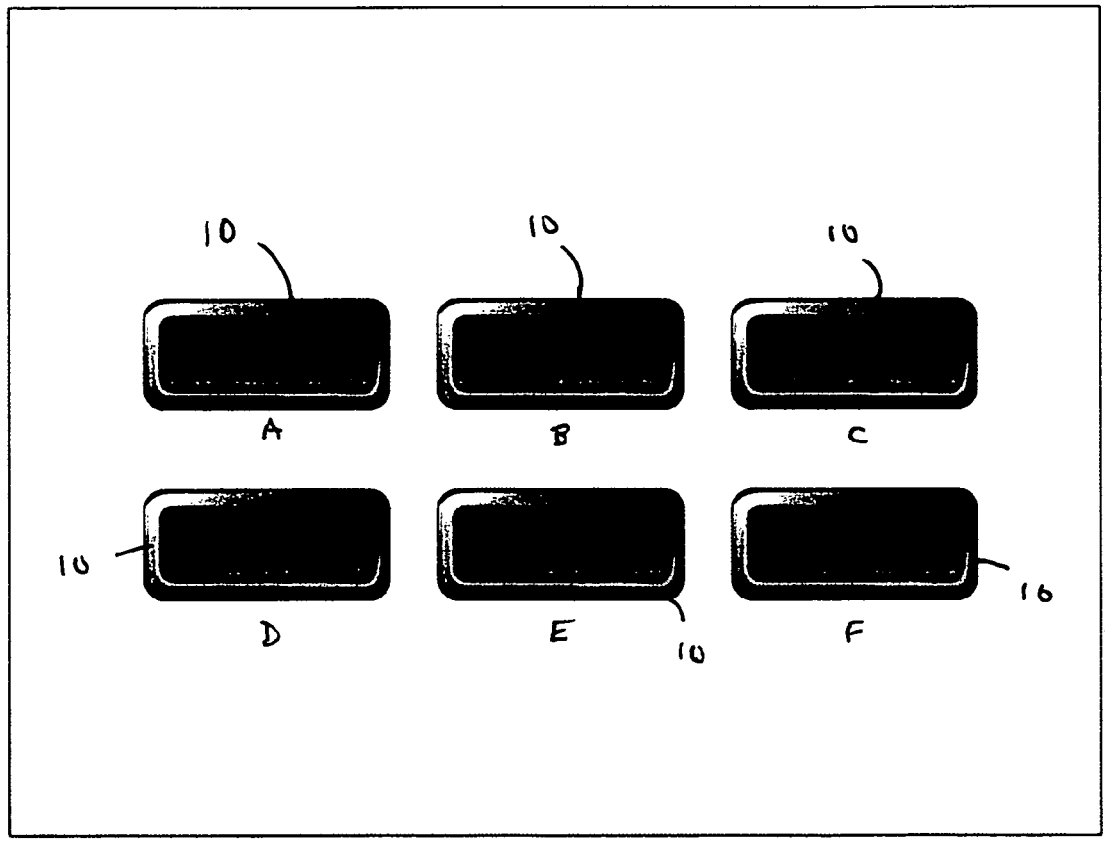
FIG. 7 illustrates a digital label with a changing serial number for authentication.

The digital label 10 can be programmed to change or update the serial number at a predetermined interval to make it more difficult to mimic. FIG. 7 illustrates a digital label 10 that has a changing serial number. In this embodiment, the digital label 10 may include an algorithm for generating the authentication number that is known only to the product manufacturer. For example, the algorithm may comprises a function that generates an authentication code based on the current time and a secret key that is stored in a secure, tamper-proof memory.

Figure 8:
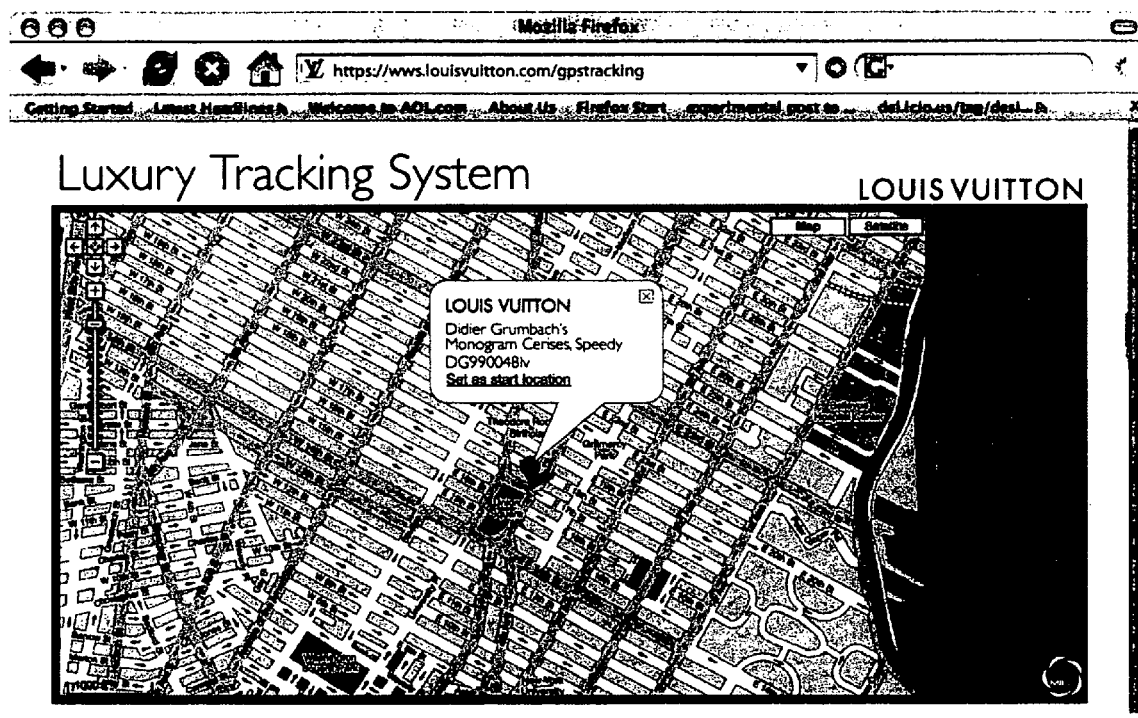
FIG. 8 illustrates a web interface for a server that product tracking services.

The tag or digital label may include a GPS system 50 to enable tracking of the product. The global positioning system in the digital label 10 can determine and record the product's location periodically. This feature can be activated, for example, when the user is traveling to keep a history of the product's movement. The product manufacturer may maintain the web-based server to track products for its registered customers. An application program in the digital label 10 can report the current position of the product to the server at predetermined time intervals or in response to predetermined events or conditions. FIG. 8 illustrates an interface for a web-based tracking system that can be accessed by the user via the Internet to track the product.

EXAMPLE 2

Product Container for Medications

Figure 9:
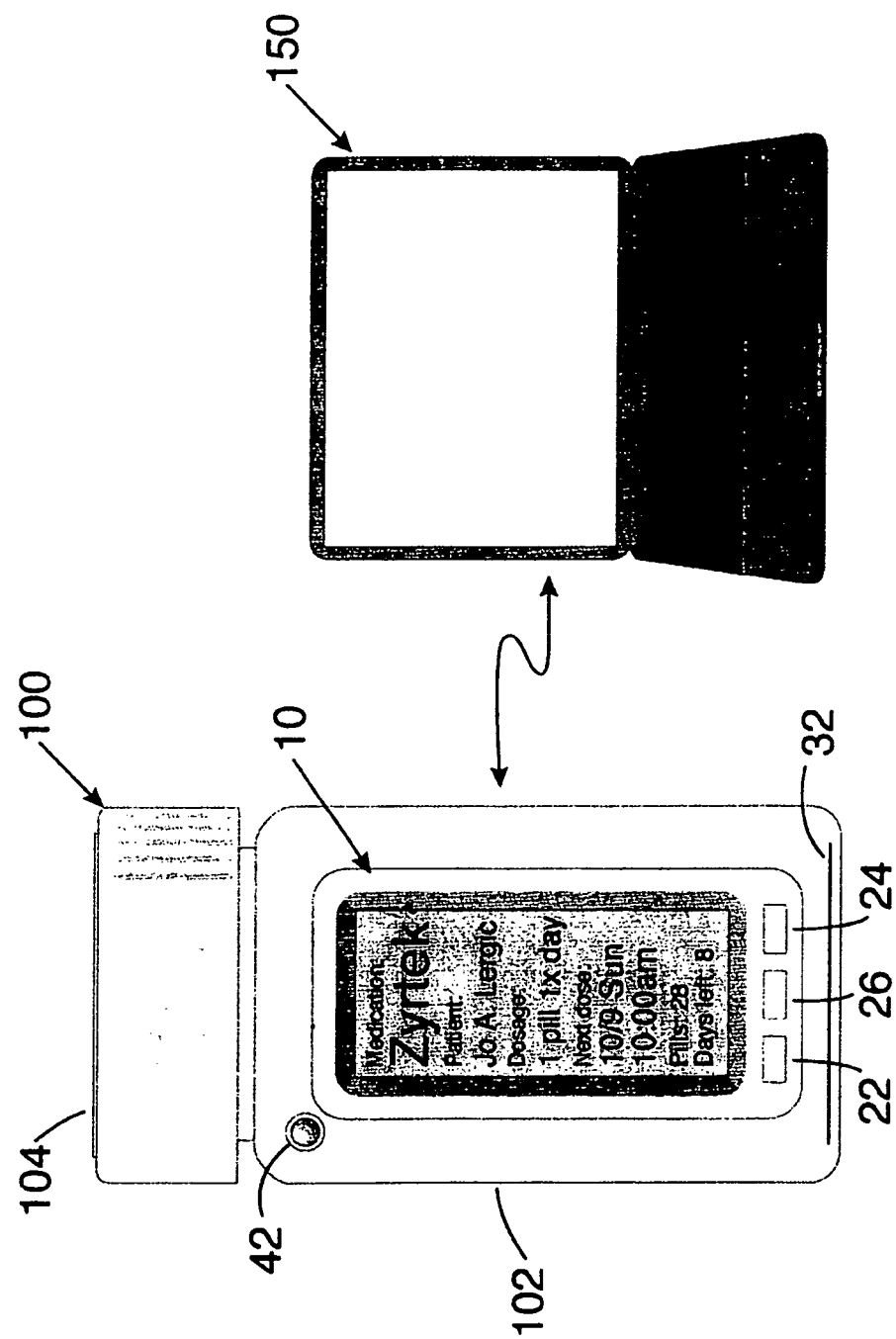
FIG. 9 is a schematic drawing of a digital label incorporated in a product container and communicating with a computer.
Figure 10:
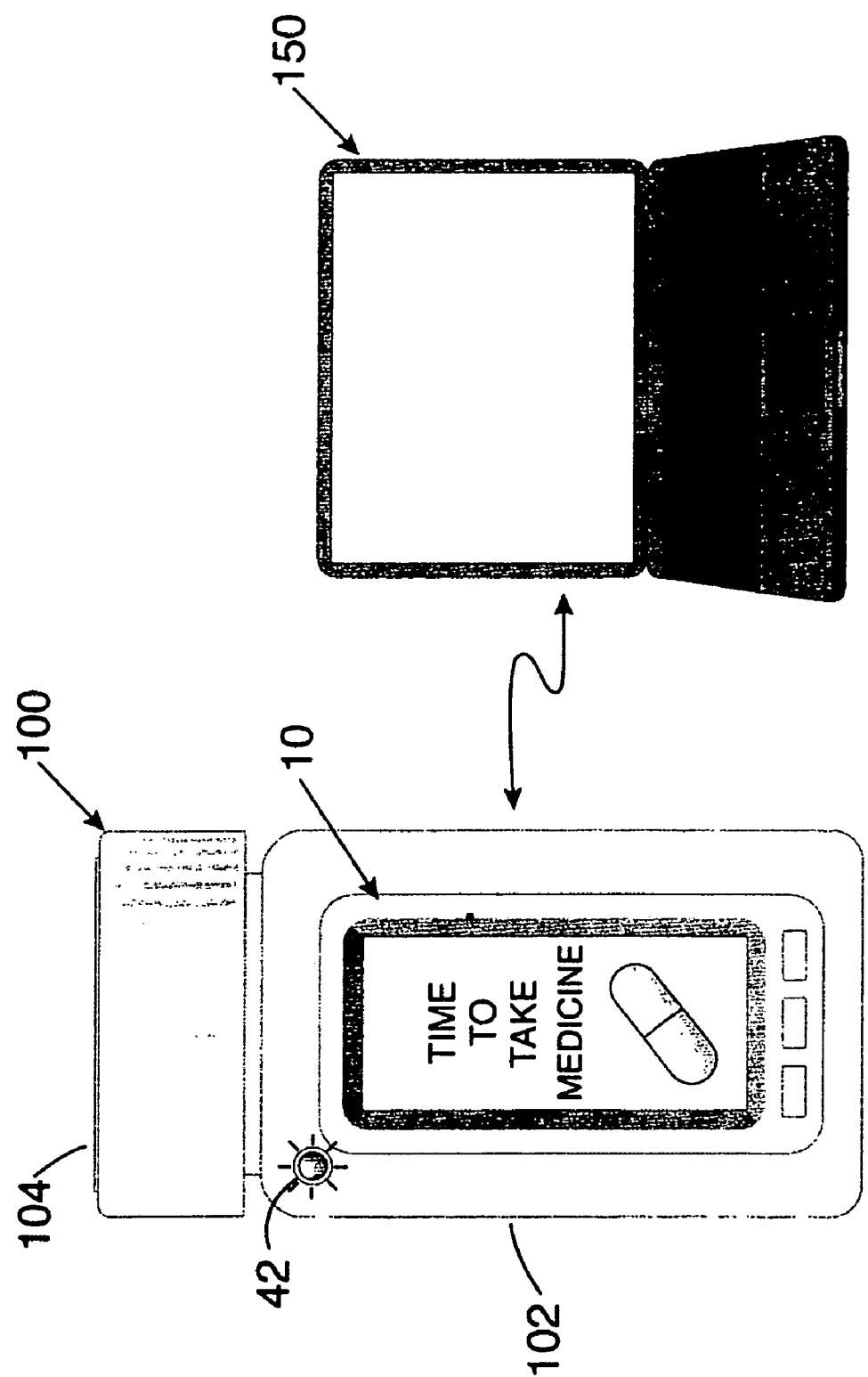
FIG. 10 is a schematic drawing of a digital label incorporated in a product container and communicating with a computer.
Figure 1:
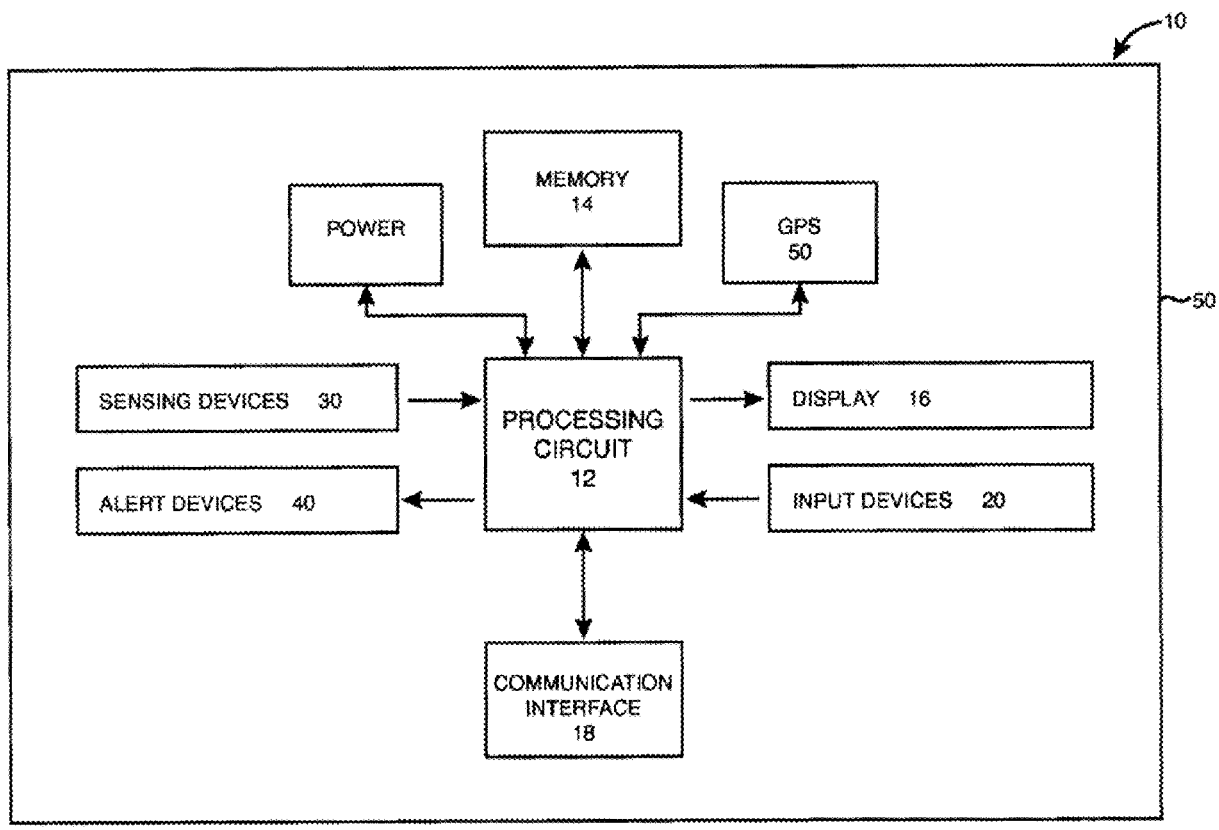
Figure 6:
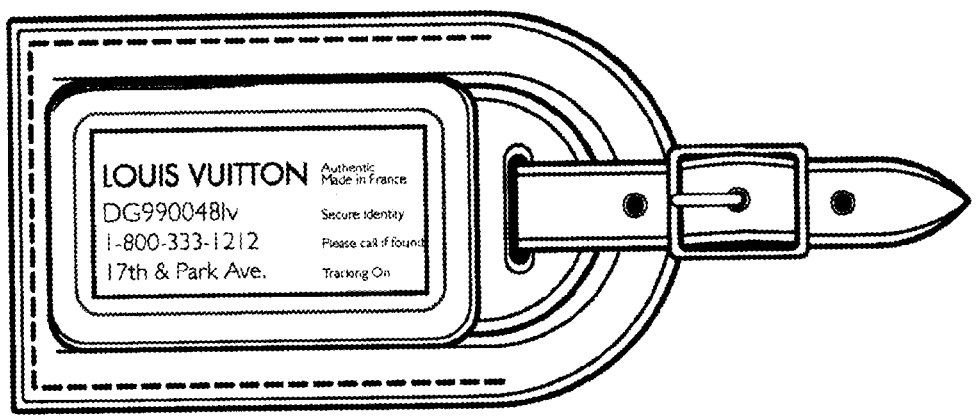
Figure 7:
Figure 8:
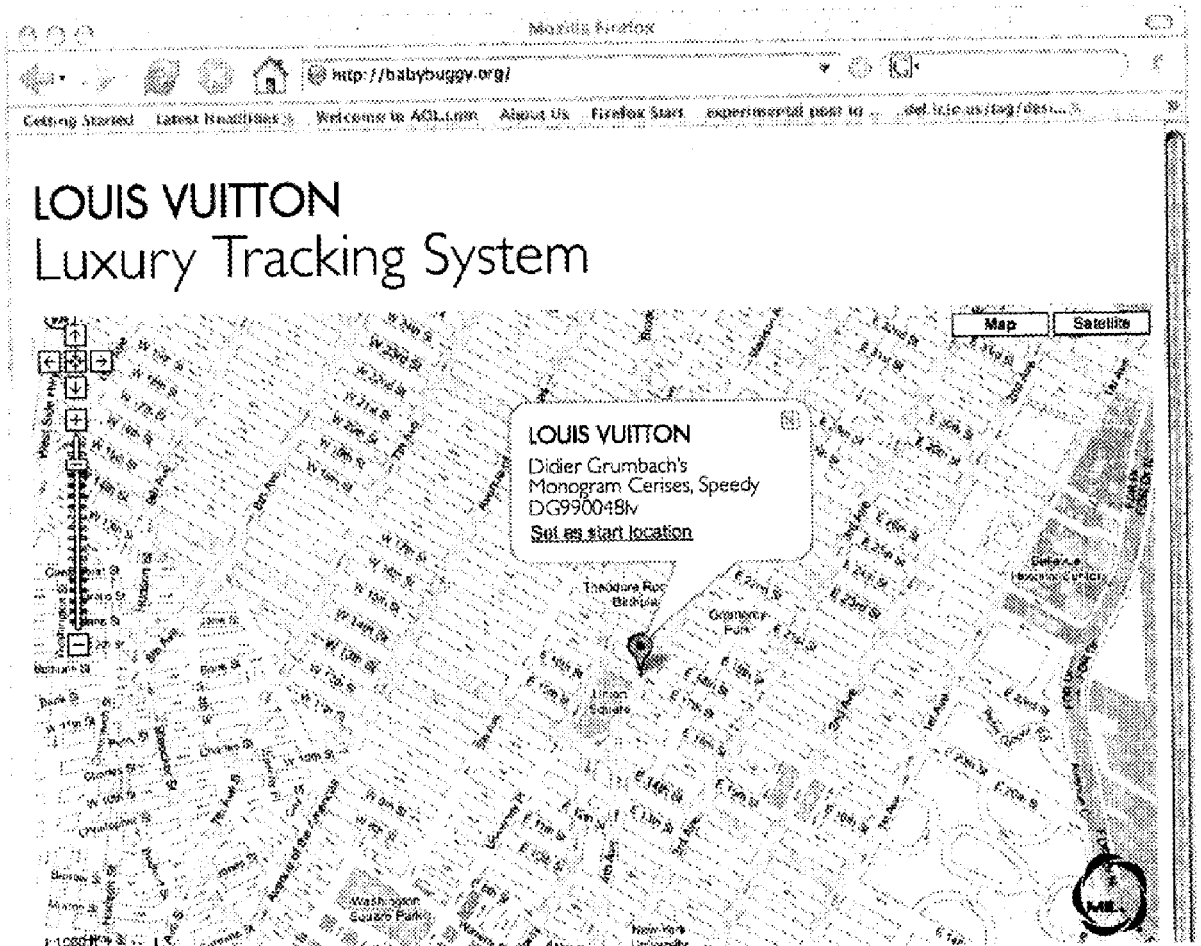
Figure 9:
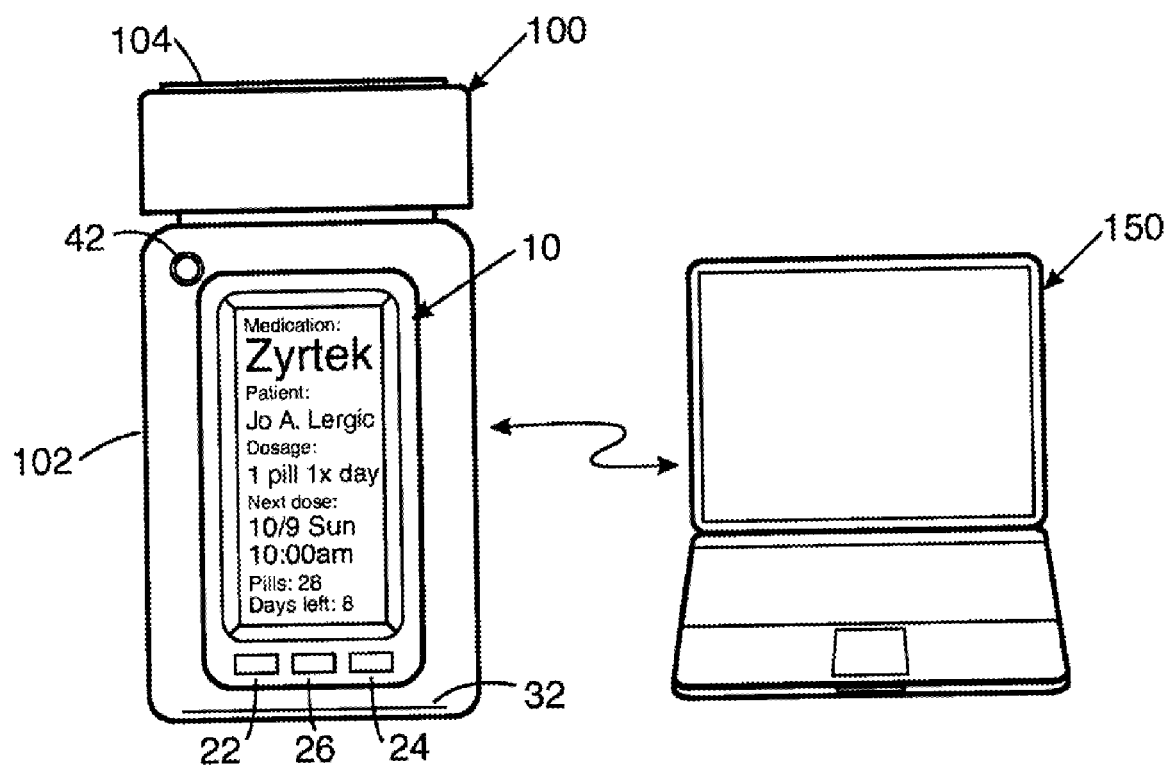
Figure 10:
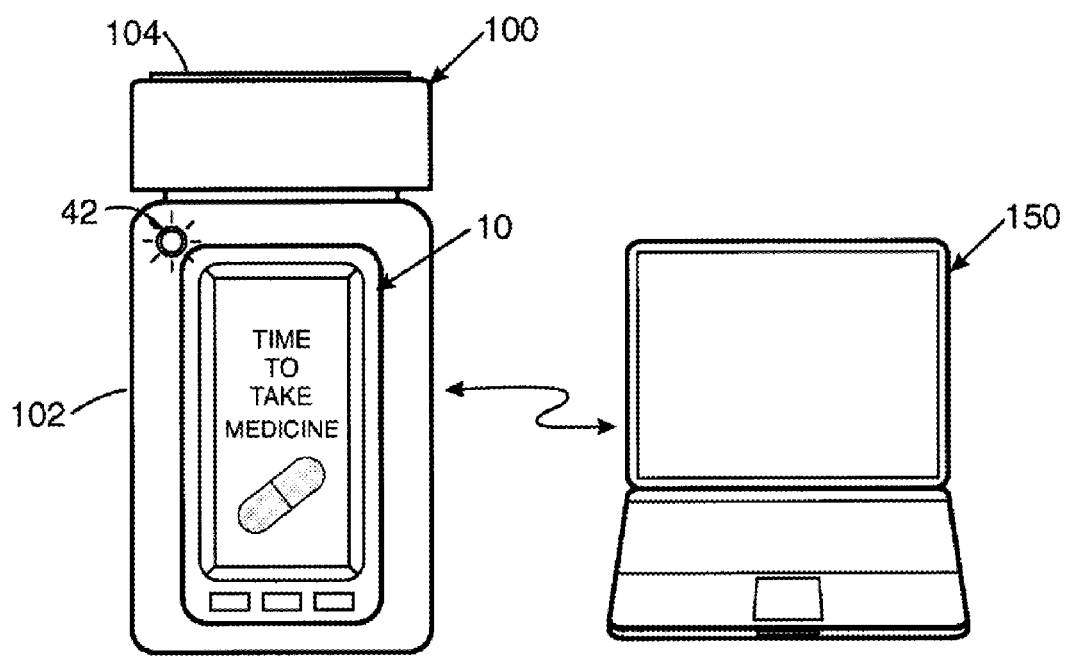

FIGS. 9 and 10 illustrate a pharmaceutical container 100 for medications including a digital label 10 according to one embodiment of the invention. The pharmaceutical container 100 comprises a bottle 102 and a cap 104. The digital label 10 is embedded in the walls of the bottle 102. The digital label 10 includes three buttons 22, 24 and 26 for receiving user input. Buttons 22 and 24 are used to navigate on-screen menus and to scroll through information on the display 16. The center button 26 is used to invoke the on-screen menu and make menu selections. The digital label 10 includes an indicator lamp 42 and weight sensor 32, which are integrated with the bottle 102. The indicator lamp 42 functions as an alerting device 40 for alerting the user when it is time to take medication as described more fully below. The weight sensor 32 located in the bottom of the product container 100 is used to detect the amount of remaining medication in the pharmaceutical container. The digital label 10 also includes a wireless communications interface 18 for communicating with remote devices, such as a computer 150.

The digital label 10 stores and displays prescription data customized for the user as well as detailed drug data. The prescription data and drug data may be uploaded from a computer 150 to the digital label 10 by the manufacturer, pharmacist, doctor, or end user. In this example, the prescription data includes the medication, patient's name, and dosage information. Drug data may include information about medications, such as ingredients and chemical composition, possible side effects and drug interactions, precautions, warnings, government regulations, legal notices, disclaimers and disclosures, notifications, medication updates, recalls, etc. Such information is typically too voluminous to print on a conventional printed label, but can be easily stored and displayed on the digital label 10. Drug information including updates could also be transmitted to a computer 150 over the communications interface 18 for viewing or printing. The digital label 10 could also communicate with a web-based server, cell phone, personal digital assistant, etc., to transmit and receive information.

An application program stored in the digital label 10 alerts the user when it is time to take medications, provides instructions on how to take medications, and records dosages taken by the user. The application program may also keep track of the remaining amount of medication and alert the user when it is time to have medications refilled. The amount of remaining medication may be determined from the input of the weight sensor 32. Alternatively, the user may manually input usage information when the user takes medication to record such event. The user can be alerted to take or refill medication by activating the indicator lamp 42 and displaying a message to the user on the display 16 as shown in FIG. 10. The digital label 10 may also, if desired, send a message to the user's cell phone or computer when it is time to take or refill medications. For example, the application may send an email or text message to the user's cell phone or computer. When it is time to refill medications, the digital label 10 may also send a notification to the user's pharmacist to avoid the need for calling in prescriptions in advance.

The application program may also collect and store usage information, such as the date and time that the medication is taken, the amount taken, the location, and environmental conditions (temperature, humidity, altitude, etc.) at the time medication is taken. Usage information may be determined based on input from the weight, temperature, humidity and other sensors 32. Alternatively, the user can manually enter and record usage information using the available user input devices 20. The usage information may be output to the display 16 or transmitted to a computer 150 or other external device, or processed along with information from other digital labels and products to coordinate multiple usage and consumption.

The application program in the digital label 10 may cooperate with or integrate with medication management software on computer 150 or other device, such as a cell phone, PDA, or web-based server system. The digital label 10 can exchange prescription data, drug data and/or user data with the computer 150 or other device. The medication management software on the computer 150 can thus keep track of all medications being taken by the user and alert the user to potential problems and provide updates to the digital label 10 when necessary. The medication management software may include a database of pharmaceutical products. The medication management software can alert the user of potentially adverse drug interactions and side effects due to combinations of medications being taken. The medication management software may also include scheduling algorithms for suggesting times to take different medications to minimize drug interactions and maximize efficacy. A medication schedule can then be generated and transferred to the digital label 10 by the medication management software. The medication management software can also store information concerning the user's diet and suggest foods and beverages that should be used or avoided. Usage information indicating the dosages taken by the user can be transferred from the digital label 10 to the medication management software for evaluation and/or storage. This medication history may be transferred or uploaded to a physician. Alternatively, the digital label 10 can store medication history for later transfer to a computer at a physician's office.

Several examples of the invention have been described. However, the present invention may be carried out in other specific ways than those herein set forth without departing from the spirit and essential characteristics of the invention. The present embodiments are, therefore, to be considered in all respects as illustrative and not restrictive, and all changes coming within the meaning and equivalency range of the appended claims are intended to be embraced therein.

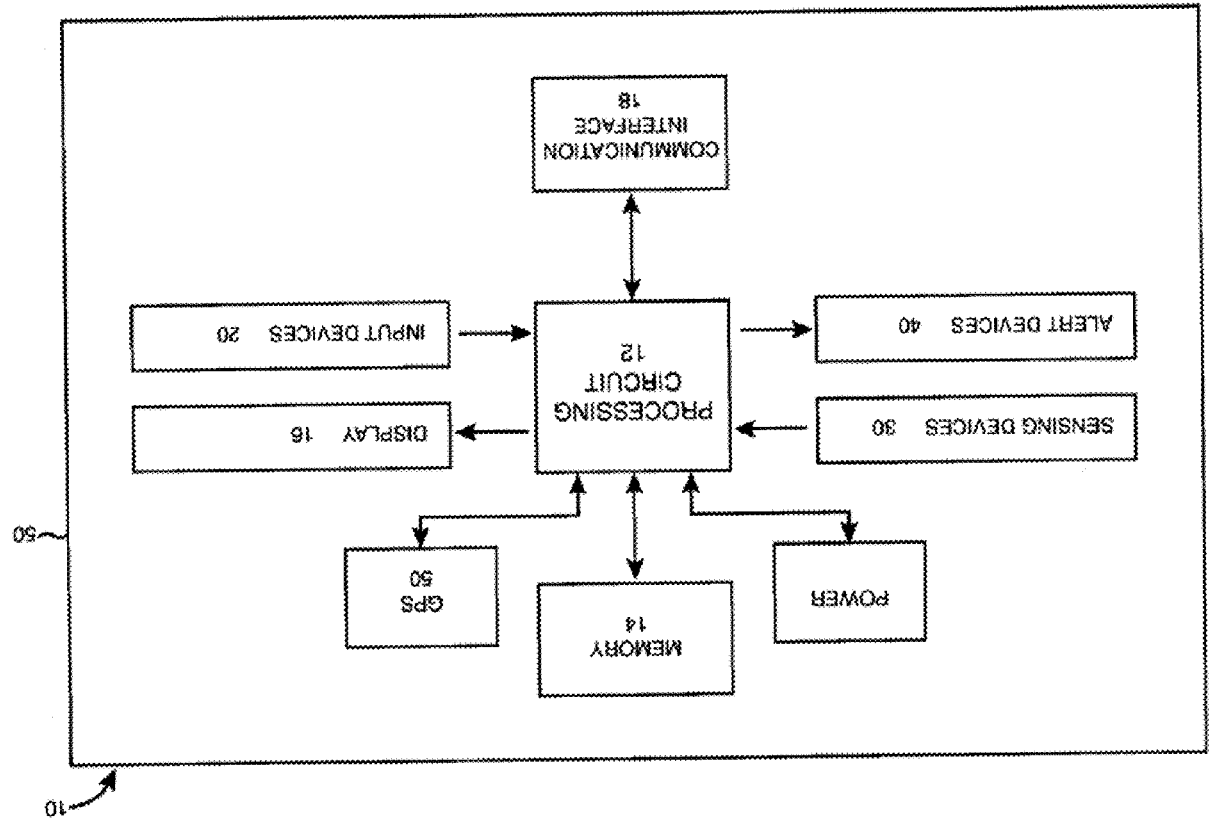

What is claimed is:

1. A label device for being affixed to a product and conveying label information to the user of the product, said label device comprising:
   a) a digital label comprising a processing circuit, a memory for storing label information, and a display for displaying label information; and
   b) an extensible program stored in said memory of said digital label and executed by said processor, said extensible program being configured to execute one or more user-defined applications.

2. The label device of claim 1 wherein said extensible program comprises an operating system program having an application interface.

3. The label device of claim 1 wherein said digital label further comprises a communications interface for communicating with a remote device.

4. The label device of claim 3 wherein the communications interface comprises a wireless interface.

5. The label device of claim 1 wherein said memory in said digital label stores user information.

6. The label device of claim 5 wherein said user information comprises usage data indicative of the use of said product.

7. The label device of claim 6 wherein said processor in said digital label is configured to output said usage information to said display.

8. The label device of claim 6 wherein said processor in said digital label is configured to exchange usage information over said communications interface with a remote device.

9. The label device of claim 1 wherein said digital label further comprises at least one input device for receiving user input.

10. The label device of claim 1 further including an alerting device controlled by said processor for generating an alert signal responsive to a predetermined event.

11. The label device of claim 10 wherein the processor is configured to activate the alerting device to notify the user of a scheduled event.

12. The label device of claim 10 further including a sensing device for generating input signals for said processor.

13. The label device of claim 12 wherein the processor is configured to activate the alerting device responsive to the detection of a predetermined condition by the sensing device.

14. The label device of claim 1 further including a location detector connected to said processor for determining a location of said digital label.

15. The label device of claim 1 wherein product authentication data is stored in said memory.

16. A method for labeling a product comprising:
   a) attaching a digital label including a processing circuit, a memory for storing label information, and a display for displaying label information;
   b) storing an extensible program in said memory for execution by said processor; and
   c) configuring the extensible program to execute one or more user-defined applications.

17. The method of claim 16 further comprising outputting label information to said display for viewing by said user.

18. The method of claim 17 further comprising storing user information in said memory of said digital label.

19. The method of claim 18 wherein said user information includes usage information indicative of the use of the product.

20. The method of claim 19 further comprising outputting usage information to said display of said digital label.

21. The method of claim 19 wherein said digital label further includes a communications interface and further comprising transferring said or usage information to a remote device.

22. The method of claim 21 wherein the communications interface comprises a wireless interface.

23. The method of claim 18 wherein the digital label further includes a location detector and wherein storing user information comprises storing location information derived from said location detector in said memory of said digital label.

24. The method of claim 18 wherein said digital label further includes at least one input device for receiving user input and further comprising receiving input of said user information by means of said user input device.

25. The method of claim 17 wherein the digital label further includes an alerting device controlled by said processor for generating an alert signal and further comprising configuring the processor to activate responsive to a predetermined event or condition.

26. The method of claim 25 wherein the processor is configured to activate the alerting device to notify the user of a scheduled event.

27. The method of claim 25 wherein the digital label further comprising a sensing device providing input to said processor and further comprising configuring the processor to activate the alerting device responsive to the detection of a predetermined condition by said sensing device.

28. The method of claim 25 further comprising storing product authentication data in said memory of said digital label.

29. A device for packaging a product comprising:
  a) a product container to contain a product;
  b) a digital label affixed to said product container and comprising a processing circuit, a memory for storing label information, and a display for displaying label information; and
  c) an extensible program stored in said memory of said digital label and executed by said processor, said extensible program being configured to execute one or more user-defined applications.

30. The device of claim 29 wherein said extensible program comprises an operating system program having an application interface.

31. The device of claim 29 wherein the communications interface comprises a wireless interface.

32. The device of claim 31 wherein said memory in said digital label stores user information.

33. The device of claim 32 wherein said user information comprises usage information indicative of the user of the product.

34. The device of claim 33 wherein said processor in said digital label is configured to output said usage information to said display.

35. The device of claim 33 wherein said processor in said digital label is configured to transfer said usage information over said communications interface to a remote device.

36. The device of claim 29 wherein said digital label further comprises at least one input device for receiving user input.

37. The device of claim 29 further including an alerting device controlled by said processor for generating an alert signal responsive to a predetermined event.

38. The device of claim 37 wherein the processor is configured to activate the alerting device to notify the user of a scheduled event.

39. The device of claim 37 further including a sensing device for generating input signals for said processor.

40. The device of claim 39 wherein the processor is configured to activate the alerting device responsive to the detection of a predetermined condition by the sensing device.

41. The device of claim 29 further including a location detector connected to said processor for determining a location of said digital label.

42. The device of claim 29 wherein product authentication data is stored in said memory.

* * * * *

UNITED STATES PATENT AND TRADEMARK OFFICE
CERTIFICATE OF CORRECTION

PATENT NO. : 7,392,953 B2 Page 1 of 8
APPLICATION NO. : 11/371530
DATED : July 1, 2008
INVENTOR(S) : Chu It is certified that error appears in the above-identified patent and that said Letters Patent is hereby corrected as shown below:

The title page should be deleted and substitute therefor the attached title page.

Replace Figs. 1, 6, 7, 8, 9, and 10 with the formal drawings attached.

Signed and Sealed this

Twenty-fifth Day of November, 2008

JON W. DUDAS
*Director of the United States Patent and Trademark Office*

(12) United States Patent
Chu

(10) Patent No.: US 7,392,953 B2
(45) Date of Patent: Jul. 1, 2008

(54) PROGRAMMABLE DIGITAL LABELS

(75) Inventor: Victor Chu, New York, NY (US)

(73) Assignee: MIL Digital Labeling, Inc., New York, NY (US)

(*) Notice: Subject to any disclaimer, the term of this patent is extended or adjusted under 35 U.S.C. 154(b) by 0 days.

(21) Appl. No.: 11/371,530

(22) Filed: Mar. 9, 2006

(65) Prior Publication Data

US 2006/0202042 A1    Sep. 14, 2006

Related U.S. Application Data

(60) Provisional application No. 60/660,500, filed on Mar. 10, 2005.

(51) Int. Cl.
   *G06K 19/06*    (2006.01)
(52) U.S. Cl. .................................. 235/492; 235/380

(58) Field of Classification Search ............... 235/487, 235/492, 380, 375
See application file for complete search history.

(56) References Cited

U.S. PATENT DOCUMENTS

| 6,753,830 | B2 | 6/2004 | Gelbman | |
| 2007/0024551 | A1* | 2/2007 | Gelbman | 345/85 |

* cited by examiner

*Primary Examiner*—Karl D. Frech
(74) *Attorney, Agent, or Firm*—Coats & Bennett, P.L.L.C.

(57) ABSTRACT

A label for a product includes an electronic display for displaying label information. The digital label includes an operating system program with an applications interface to allow development of custom applications by manufacturers, retailers, and users of the product. The digital label also includes a communications interface enable communication with external devices, such as other computer systems. The processor in the digital label can process, display, and transmit information.

42 Claims, 9 Drawing Sheets